US011414407B2

(12) United States Patent
Marcotulli et al.

(10) Patent No.: US 11,414,407 B2
(45) Date of Patent: Aug. 16, 2022

(54) CRYSTALLINE FORMS OF NICOTINAMIDE RIBOSIDE CHLORIDE

(71) Applicant: Elysium Health, Inc., New York, NY (US)

(72) Inventors: Eric Marcotulli, New York, NY (US); Dan Alminana, New York, NY (US); Ryan Dellinger, Azusa, CA (US); Mark Morris, New York, NY (US)

(73) Assignee: Elysium Health, Inc., New York, NY (US)

( * ) Notice: Subject to any disclaimer, the term of this patent is extended or adjusted under 35 U.S.C. 154(b) by 0 days.

(21) Appl. No.: 16/955,412

(22) PCT Filed: Dec. 20, 2018

(86) PCT No.: PCT/US2018/066769
§ 371 (c)(1),
(2) Date: Jun. 18, 2020

(87) PCT Pub. No.: WO2019/126482
PCT Pub. Date: Jun. 27, 2019

(65) Prior Publication Data
US 2021/0094936 A1    Apr. 1, 2021

Related U.S. Application Data

(60) Provisional application No. 62/609,512, filed on Dec. 22, 2017.

(51) Int. Cl.
*C07D 405/04* (2006.01)

(52) U.S. Cl.
CPC ........ *C07D 405/04* (2013.01); *C07B 2200/13* (2013.01)

(58) Field of Classification Search
CPC .................................................. C07H 19/048
See application file for complete search history.

(56) References Cited

U.S. PATENT DOCUMENTS

| | | | |
|---|---|---|---|
| 3,708,394 A | 1/1973 | Nakayama | |
| 3,728,111 A | 4/1973 | Stromblad et al. | |
| 6,627,646 B2 * | 9/2003 | Bakale | A61P 37/08 514/322 |
| 7,776,326 B2 | 8/2010 | Milbrandt et al. | |
| 8,106,184 B2 | 1/2012 | Sauve et al. | |
| 8,114,626 B2 | 2/2012 | Brenner et al. | |
| 8,197,807 B2 | 6/2012 | Brenner | |
| 8,217,006 B2 | 7/2012 | Stamler et al. | |
| 8,383,086 B2 | 2/2013 | Brenner | |
| 8,399,489 B2 | 3/2013 | Basarab et al. | |
| 8,481,711 B2 | 7/2013 | Kaminishi et al. | |
| 8,507,251 B2 | 8/2013 | Greenstein | |
| 9,000,147 B2 | 4/2015 | Sauve et al. | |
| 10,000,519 B2 | 6/2018 | Migaud et al. | |
| 10,189,872 B2 | 1/2019 | Carlson et al. | |
| 2004/0266723 A1 | 12/2004 | Otto et al. | |
| 2005/0020587 A1 | 1/2005 | Bailey et al. | |
| 2005/0267023 A1 | 12/2005 | Sinclair et al. | |
| 2006/0229265 A1 | 10/2006 | Milburn et al. | |
| 2007/0149466 A1 | 6/2007 | Milburn et al. | |
| 2007/0166296 A1 | 7/2007 | Burke et al. | |
| 2007/0248590 A1 | 10/2007 | Milne et al. | |
| 2008/0146569 A1 | 6/2008 | Blake et al. | |
| 2010/0015072 A1 | 1/2010 | Polla et al. | |
| 2010/0047177 A1 | 2/2010 | Milbrandt et al. | |
| 2010/0279973 A1 | 11/2010 | Chun et al. | |
| 2011/0065662 A1 | 3/2011 | Rinsch et al. | |
| 2011/0306597 A1 | 12/2011 | Crawforth et al. | |
| 2012/0022013 A1 | 1/2012 | Sinclair et al. | |
| 2012/0107888 A1 | 5/2012 | Schmalisch et al. | |
| 2012/0172584 A1 | 7/2012 | Sauve et al. | |
| 2012/0328526 A1 | 12/2012 | Kristian | |
| 2012/0329748 A1 | 12/2012 | Sauve et al. | |
| 2013/0165398 A1 | 6/2013 | Huber | |
| 2014/0045874 A1 | 2/2014 | Tolleth et al. | |
| 2014/0065099 A1 | 3/2014 | Alvarez et al. | |
| 2014/0221319 A1 | 8/2014 | Sinclair et al. | |
| 2014/0256760 A1 | 9/2014 | Tolleth et al. | |
| 2014/0364441 A1 | 12/2014 | Wei et al. | |
| 2015/0056274 A1 | 2/2015 | Zemel et al. | |
| 2015/0118169 A1 | 4/2015 | Hakozaki et al. | |
| 2015/0132280 A1 | 5/2015 | Lopez et al. | |
| 2015/0133396 A1 | 5/2015 | Sinclair et al. | |
| 2015/0174148 A1 | 6/2015 | Brown et al. | |

(Continued)

FOREIGN PATENT DOCUMENTS

| | | |
|---|---|---|
| CA | 2437994 C | 5/2011 |
| EP | 0981534 B1 | 5/2006 |

(Continued)

OTHER PUBLICATIONS

CMU Pharmaceutical polymorphism, internet p. 1-3 (2002) printout Apr. 3, 2008.*
Singhal et al., "Drug Polymorphism, etc.," Advanced Drug Delivery reviews 56, p. 335-347 (2004).*
Concise Encyclopedia Chemistry, NY: Walter de Gruyter, 1993, 872-873.*
Jain et al., "Polymorphism in Pharmacy", Indian Drugs, 1986, 23(6) 315-329.*
Muzaffar et al., "Polymorphism and Drug Availability, etc.," J of Pharm. (Lahore), 1979, 1(1),59-66.*
U.S. Pharmacopia #23, National Formulary#18, 1995, 1843-1844.*
Doelker, english translation of S.T.P, Pratiques (1999), 9(5), 399-409, pp. 1-33.*
Doelker, english translation of Ann. Pharm. Fr., 2002, 60: 161-176, pp. 1-39.*

(Continued)

*Primary Examiner* — Layla D Berry
(74) *Attorney, Agent, or Firm* — Foley Hoag LLP; Brendan T. Jones; Laura A. Wzorek

(57) ABSTRACT

Provided herein are crystalline forms of nicotinamide riboside chloride and methods of making the same. Also provided are compositions comprising the crystalline form of nicotinamide riboside chloride, and therapeutic methods employing the crystalline form of nicotinamide riboside chloride.

14 Claims, 7 Drawing Sheets

(56) References Cited

U.S. PATENT DOCUMENTS

| | | | |
|---|---|---|---|
| 2015/0175645 | A1 | 6/2015 | Milburn et al. |
| 2015/0297508 | A1 | 10/2015 | Andriette |
| 2016/0008329 | A1 | 1/2016 | Zemel et al. |
| 2017/0204131 | A1 | 7/2017 | Szczepankiewicz et al. |
| 2017/0296564 | A1 | 10/2017 | Dellinger et al. |
| 2021/0094936 | A1 | 4/2021 | Marcotulli et al. |

FOREIGN PATENT DOCUMENTS

| | | | |
|---|---|---|---|
| WO | WO-2006/105440 | A2 | 10/2006 |
| WO | WO-2007/136744 | A1 | 11/2007 |
| WO | WO-2011/005289 | A2 | 1/2011 |
| WO | WO-2013/085555 | A2 | 6/2013 |
| WO | WO-2014/059029 | A1 | 4/2014 |
| WO | WO-2014/111906 | A1 | 7/2014 |
| WO | WO-2015/014722 | A1 | 2/2015 |
| WO | WO-2015/064988 | A1 | 5/2015 |
| WO | WO-2015/066382 | A1 | 5/2015 |
| WO | WO-2015/099842 | A1 | 7/2015 |
| WO | WO-2015/138969 | A1 | 9/2015 |
| WO | WO-2015/186068 | A1 | 12/2015 |
| WO | WO-2016/011360 | A1 | 1/2016 |
| WO | WO-2016/144660 | A1 | 9/2016 |
| WO | WO-2017/218580 | A1 | 12/2017 |
| WO | WO-2018/089830 | A1 | 5/2018 |
| WO | WO-2019/126482 | A1 | 6/2019 |
| WO | WO-2021/013795 | A2 | 1/2021 |

OTHER PUBLICATIONS

Taday et al., "Using Terahertz, etc.," J of Pharm. Sci., 92(4), 2003, 831-838.*

Otuska et al., "Effect of Polymorphic, etc.," Chem. Pharm. Bull., 47(6) 852-856 (1999).*

Bedlack et al. "ALSUntangled 42, etc.," Amyotrophic Lateral Sclerosis and Frontotemporal Degeneration, 19: 317-319. (Year: 2018).*

Layzer et al., "Section Five, etc.," Cecil Textbook of Medicine, 20th ed., 2, pp. 2050-2057. (Year: 1996).*

Halebian et al., "Pharmaceutical Applications, etc.," Pharmacuetical Sciences 58(8), 911-929. (Year: 1969).*

Kirk-Othmer Encyclopedia of Chemical Technology, 8, pp. 95-147. (Year: 2002).*

International Search Report and Written Opinion for International Application No. PCT/US18/66769 dated Mar. 5, 2019.

Alvarez et al., "Nicotinamide Riboside Derivatives: Single Crystal Growth and Determination of X-ray Structures," Crystal Growth & Design, 19: 4019-4028 (2019).

Alvarez et al., "Nicotinamide Riboside Derivatives: Single Crystal Growth and Determination of X-ray Structures," University of Zurich: 24 pages (2019).

Biosynth Carbosynth., "Nicotinamide Riboside crystals and X-ray structure revealed," Carbosynth Ltd: 4 pages (2019).

Caira., "Crystalline Polymorphism of Organic Compounds," Topics in Current Chemistry, 198: 164-208(1998).

Chi et al., "Nicotinamide Riboside, a trace nutrient in foods, is a Vitamin B3 with effects on energy metabolism and neuroprotection," Current Opinion in Clinical Nutrition and Metabolic Care, 16:657-661 (2013).

ChromaDex Corporation., "High Performance Nutrition Introduces a New Product, N(R), Featuring NIAGEN™ to Support Neuroprotection in Contact Sports," ChromaDex Press Release dated Jun. 25, 2013 (4 pages).

ChromaDex Corporation., "Life Extension Introduces a New Anti-Aging Supplement, NAD+ Cell Regenerator™, Featuring NIAGEN™," ChromaDex Press Release dated Oct. 1, 2014 (4 pages).

ChromaDex Corporation., "Results from First Human Clinical Study Demonstrate ChromaDex's Niagen(R) Nicotinamide Riboside Effectively Increase the Co-enyzme NAD+ and is Safe," ChromaDex Investor Resources News: 4 pages (2015).

Clapper et al., "Pyridine Nucleotide Metabolites Stimulate Calcium Release from Sea Urchin Egg Microsomes Desensitized to Inositol Trisphosphate," The Journal of Biological Chemistry, 262(20): 9561-9568 (1987).

Daniells., "Chromadex CEO: We think Niagen has a much bigger market, like omega-3," NutraIngredients: 3 pages (2014).

Elysium's Preliminary Invalidity Contentions: *W. R. Grace & Co.-Conn.* vs. *Elysium Health, Inc.*; United States District Court for the District of Delaware: 33 pages (2021).

Franchetti et al., "Stereoselective synthesis of nicotinamide β-riboside and nucleoside analogs," Bioorganic & Medicinal Chemistry Letters, 14: 4655-4658 (2004).

Gelin et al., "Screening and In Situ Synthesis Using Crystals of a NAD Kinase Lead to a Potent Antistaphylococcal Compound," Structure, 20(6): 1107-1117 (2012).

Haigis et al., "Mammalian Sirtuins: Biological Insights and Disease Relevance," Annual Review of Pathology: Mechanisms of Disease, 5: 253-295 (2010).

Longecity., "Nicotinamide Riboside (NR/Niagen) personal experience thread," LongeCity Advocacy & Research for Unlimited Lifespans: 21 pages (2014).

Magni et al., "Enzymology of NAD homeostasis in man," Cellular and Molecular Life Sciences, 61: 19-34 (2004).

Natural Products Insider., "Thorne Launches NiaCel Featuring NIAGEN fromChromaDex," retrieved online <https:www.naturalproductinsider.com/print/14327>: 1 page (2014).

Schabert et al., "New Crystalline Salts of Nicotinamide Riboside as Food Additives," Molecules, 26: 18 pages (2021).

Sun et al., "Crystal Structure of Perakine Reductase, Founding Member of a Novel Aldo-Keto Reductase (AKR) Subfamily That Undergoes Unique Conformational Changes during NADPH Binding," Journal of Biological Chemistry: 30 pages (2012).

Tanimori et al., "An Efficient Chemical Synthesis of Nicotinamide Riboside (NAR) and Analogues," Bioorganic & Medicinal Chemistry Letters, 12: 1135-1137 (2002).

Weilgus-Kutrowska et al., "Nicotinamide riboside, an unusual, non-typical, substrate of purified purine-nucleoside phosphorylases," Eur. J. Biochem., 243: 408-414 (1997).

Yang et al., "Syntheses of Nicotinamide Riboside and Derivatives: Effective Agents for Increasing Nicotinamide Adenine Dinucleotide Concentrations in Mammalian Cells," Journal of Medicinal Chemistry, 50(26): 6458-6461 (2007).

Zhang et al., "Synthesis of Methyl 1-(2,3,5-Tri-0-acetyl-?-L-ribofuranosyl)-1,2,4-triazole-3-carboxylate from L-Ribose: From a Laboratory Procedure to a Manufacturing Process," Organic Process Research & Development, 9: 583-592 (2005).

Extended European Search Report for EP Application No. 18892817 dated Sep. 21, 2021.

\* cited by examiner

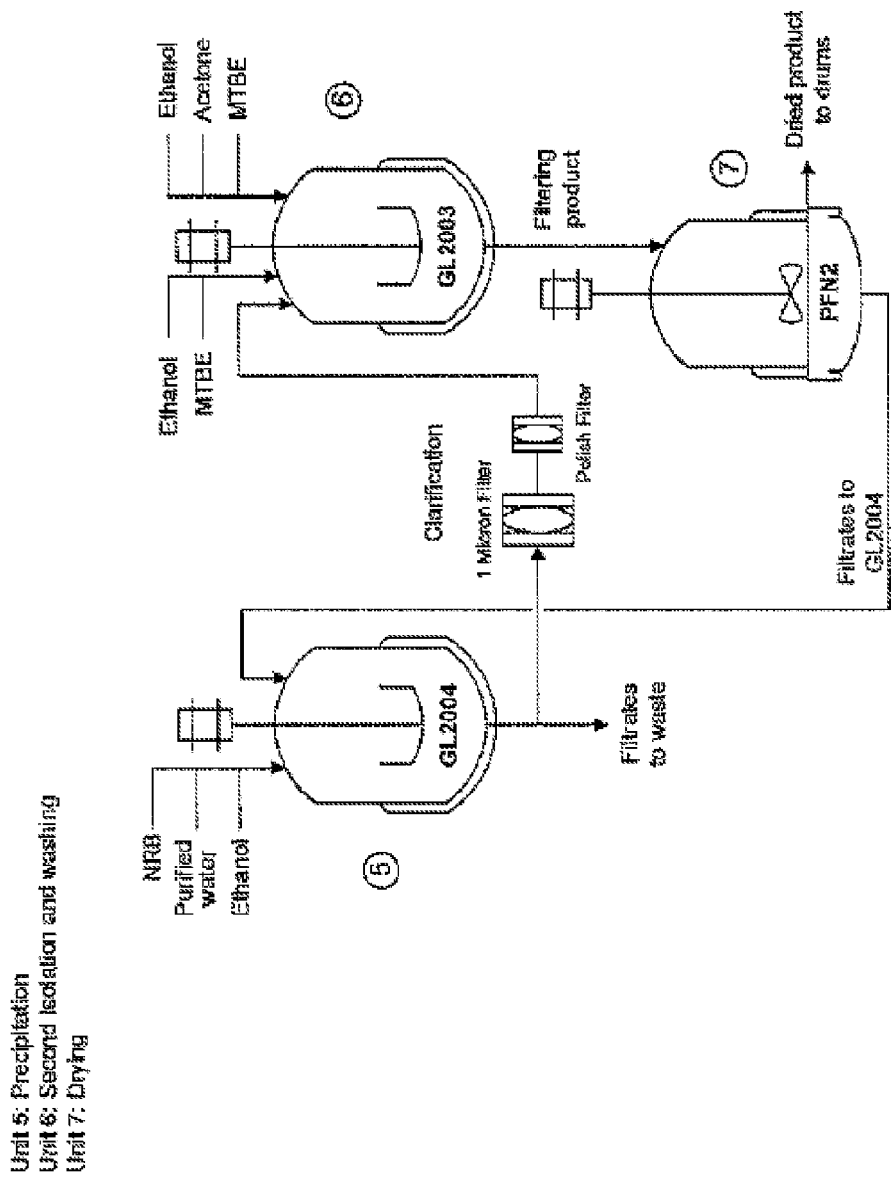
FIG. 6, continued

CRYSTALLINE FORMS OF NICOTINAMIDE RIBOSIDE CHLORIDE

RELATED APPLICATIONS

This application is a U.S. National Stage Application of International Application No. PCT/US18/66769, filed Dec. 20, 2018; which claims the benefit of priority to U.S. Provisional Patent Application Ser. No. 62/609,512, filed Dec. 22, 2017, both of which are hereby incorporated by reference in their entireties.

BACKGROUND OF THE INVENTION

Nicotinamide riboside is a pyridine-nucleoside form of niacin (i.e., vitamin B3) that serves as a precursor to nicotinamide adenine dinucleotide ($NAD^+$). $NAD^+$ promotes cellular metabolism, mitochondrial function, and energy production. Currently, nicotinamide riboside is made through synthetic methods or fermentation processes. Because of its significant potential to confer health benefits when used as a dietary supplement, there exists a need to develop highly efficient and scalable processes for the manufacture and purification of nicotinamide riboside.

SUMMARY OF THE INVENTION

In certain aspects, the present invention provides a crystalline form of a compound having the structure of formula (I):

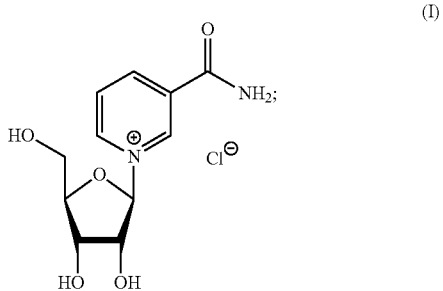

wherein the crystalline form is characterized by 2θ values of 20.9±0.1, 21.6±0.1, 21.8±0.1, 23.6±0.1, and 24.4±0.1.

In certain aspects, the present invention provides a pharmaceutical composition comprising a crystalline form of the invention in combination with a pharmaceutically acceptable carrier.

In some aspects, the invention provides a method for preparing a crystalline form of the invention, the method comprising the steps of (a) providing a mixture of a compound of formula (I) in a first organic solvent; and (b) crystallizing the compound of formula (I) from the mixture of a compound of formula (I) in a first organic solvent.

In certain aspects, the present invention provides a method of improving cellular health in a subject, comprising administering to the subject a therapeutically effective amount of a crystalline form of the invention In certain aspects, the present invention provides a method of improving sleep quality, stimulating or increasing REM sleep, or treating or preventing insomnia, desynchronosis, or a circadian rhythm sleep disorder in a subject, comprising administering to the subject a therapeutically effective amount of a crystalline form of the invention.

In certain aspects, the present invention provides a method of treating or preventing a motor neuron disease or ALS, or slowing or reversing the progression of motor neuron degeneration in a subject, comprising administering to the subject a therapeutically effective amount of a crystalline form of the invention.

In certain aspects, the present invention provides a method of improving fertility, treating or preventing infertility, inducing ovulation, increasing sperm count, or increasing lactation, comprising administering to the subject a therapeutically effective amount of a crystalline form of the invention.

In certain aspects, the present invention provides a method of treating or preventing kidney damage, acute kidney injury, or kidney disease, or increasing blood flow to the kidneys, comprising administering to the subject a therapeutically effective amount of a crystalline form of the invention.

In certain aspects, the present invention provides a method of treating or preventing liver damage or fatty liver, or decreasing the serum level of alanine transaminase (ALT) or aspartate transaminase (AST) in a subject, comprising administering to the subject a therapeutically effective amount of a crystalline form of the invention.

DETAILED DESCRIPTION OF THE INVENTION

I. Definitions

Figure 1:
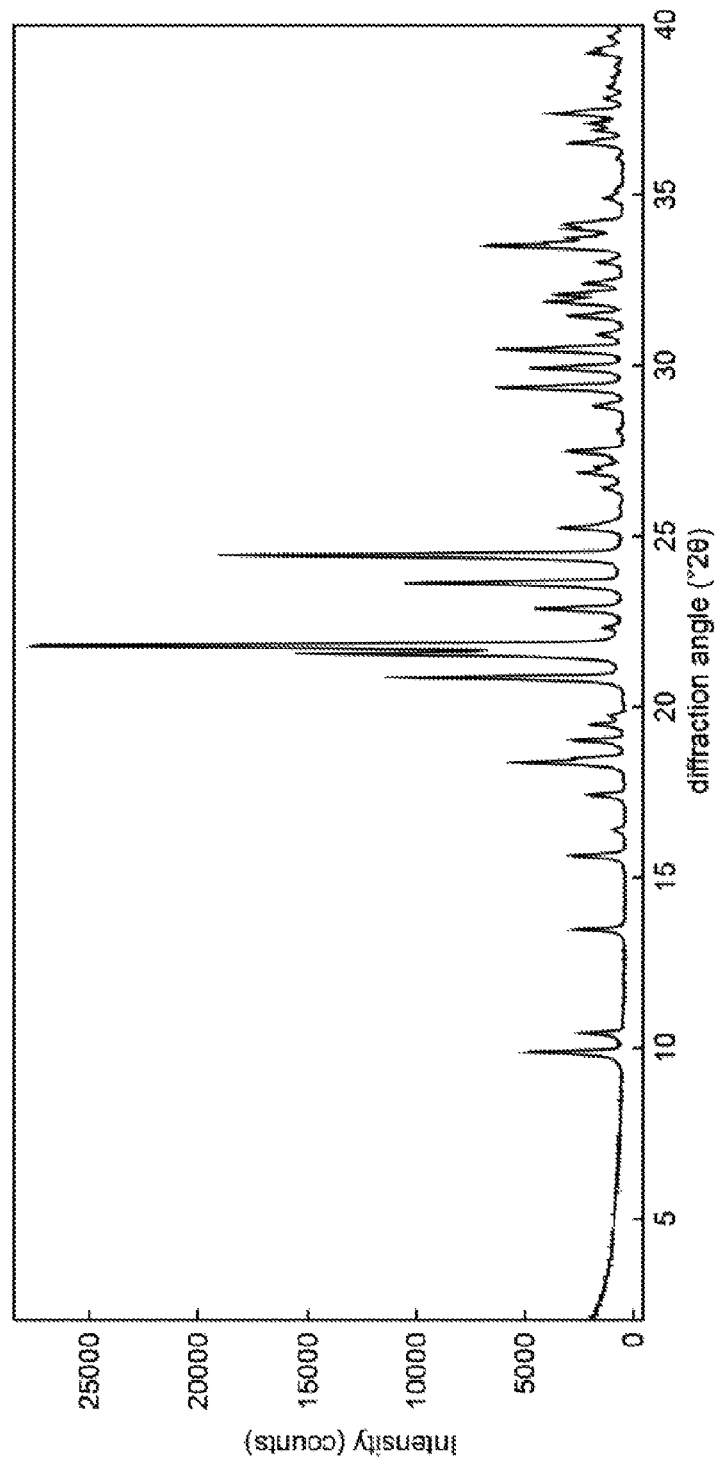
FIG. 1 shows an x-ray diffraction spectrum of the crystalline nicotinamide riboside chloride.

As used herein, the term "administering" means providing a pharmaceutical agent or composition to a subject, and includes, but is not limited to, administering by a medical professional and self-administering. Administration of a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

The phrase "pharmaceutically-acceptable carrier" as used herein means a pharmaceutically-acceptable material, composition or vehicle, such as a liquid or solid filler, diluent, excipient, or solvent encapsulating material.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

As used herein, a therapeutic that "prevents" a disorder or condition refers to a compound that, when administered to a statistical sample prior to the onset of the disorder or condition, reduces the occurrence of the disorder or condition in the treated sample relative to an untreated control sample, or delays the onset or reduces the severity of one or more symptoms of the disorder or condition relative to the untreated control sample.

II. Crystal Forms

The present invention is based on the surprising discovery of a new crystalline form of nicotinamide riboside chloride having excellent purity and ease of manufacture. Accordingly, in certain embodiments, the invention provides a crystalline form of a compound having the structure of formula (I):

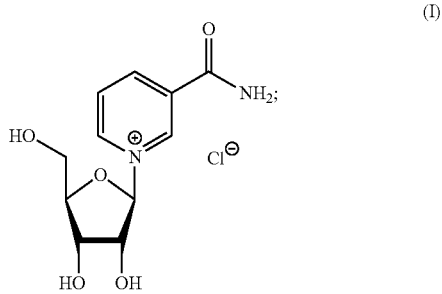

wherein the crystalline form is characterized by 2θ values of 20.9±0.1, 21.6±0.1, 21.8±0.1, 23.6±0.1, and 24.4±0.1.

In further embodiments, the crystalline form of the invention is characterized by 2θ values of 9.9±0.1, 18.4±0.1, 20.9±0.1, 21.6±0.1, 21.8±0.1, 23.6±0.1, 24.4±0.1, 29.4±0.1, 29.9±0.1, 30.5±0.1, and 33.5±0.1.

In yet further embodiments, the crystalline form of the invention is characterized by 2θ values of 9.9±0.1, 18.4±0.1, 20.9±0.1, 21.6±0.1, 21.8±0.1, 22.9±0.1, 23.6±0.1, 24.4±0.1, 25.2±0.1, 29.4±0.1, 29.9±0.1, 30.5±0.1, 31.9±0.1, 32.1±0.1, 33.5±0.1, 34.1±0.1, and 37.4±0.1.

In still yet further embodiments, the crystalline form of the invention is characterized by 2θ values of 9.9±0.1, 15.6±0.1, 18.4±0.1, 18.5±0.1, 19.0±0.1, 20.9±0.1, 21.6±0.1, 21.8±0.1, 22.9±0.1, 23.6±0.1, 24.4±0.1, 25.2±0.1, 29.4±0.1, 29.9±0.1, 30.5±0.1, 31.5±0.1, 31.9±0.1, 32.1±0.1, 33.5±0.1, 34.0±0.1, 34.1±0.1, 36.5±0.1, and 37.4±0.1.

In some embodiments, the crystalline form of the invention is characterized by 2θ values of 20.87±0.10, 21.55±0.10, 21.79±0.10, 23.63±0.10, and 24.44±0.10.

In further such embodiments, the crystalline form of the invention is characterized by 2θ values of 9.87±0.10, 18.36±0.10, 20.87±0.10, 21.55±0.10, 21.79±0.10, 23.63±0.10, 24.44±0.10, 29.35±0.10, 29.93±0.10, 30.47±0.10, and 33.51±0.10.

In yet further such embodiments, the crystalline form of the invention is characterized by 2θ values of 9.87±0.10, 18.36±0.10, 20.87±0.10, 21.55±0.10, 21.79±0.10, 22.87±0.10, 23.63±0.10, 24.44±0.10, 25.25±0.10, 29.35±0.10, 29.93±0.10, 30.47±0.10, 31.87±0.10, 32.08±0.10, 33.51±0.10, 34.15±0.10, and 37.38±0.10.

In still yet further embodiments, the crystalline form of the invention is characterized by 2θ values 9.87±0.10, 15.61±0.10, 18.36±0.10, 18.49±0.10, 19.01±0.10, 20.87±0.10, 21.55±0.10, 21.79±0.10, 22.87±0.10, 23.63±0.10, 24.44±0.10, 25.25±0.10, 29.35±0.10, 29.93±0.10, 30.47±0.10, 31.46±0.10, 31.87±0.10, 32.08±0.10, 33.51±0.10, 34.00±0.10, 34.15±0.10, 36.53±0.10, and 37.38±0.10.

The crystalline form of the invention may have an XRD spectrum substantially as shown in FIG. 1.

Figure 2:
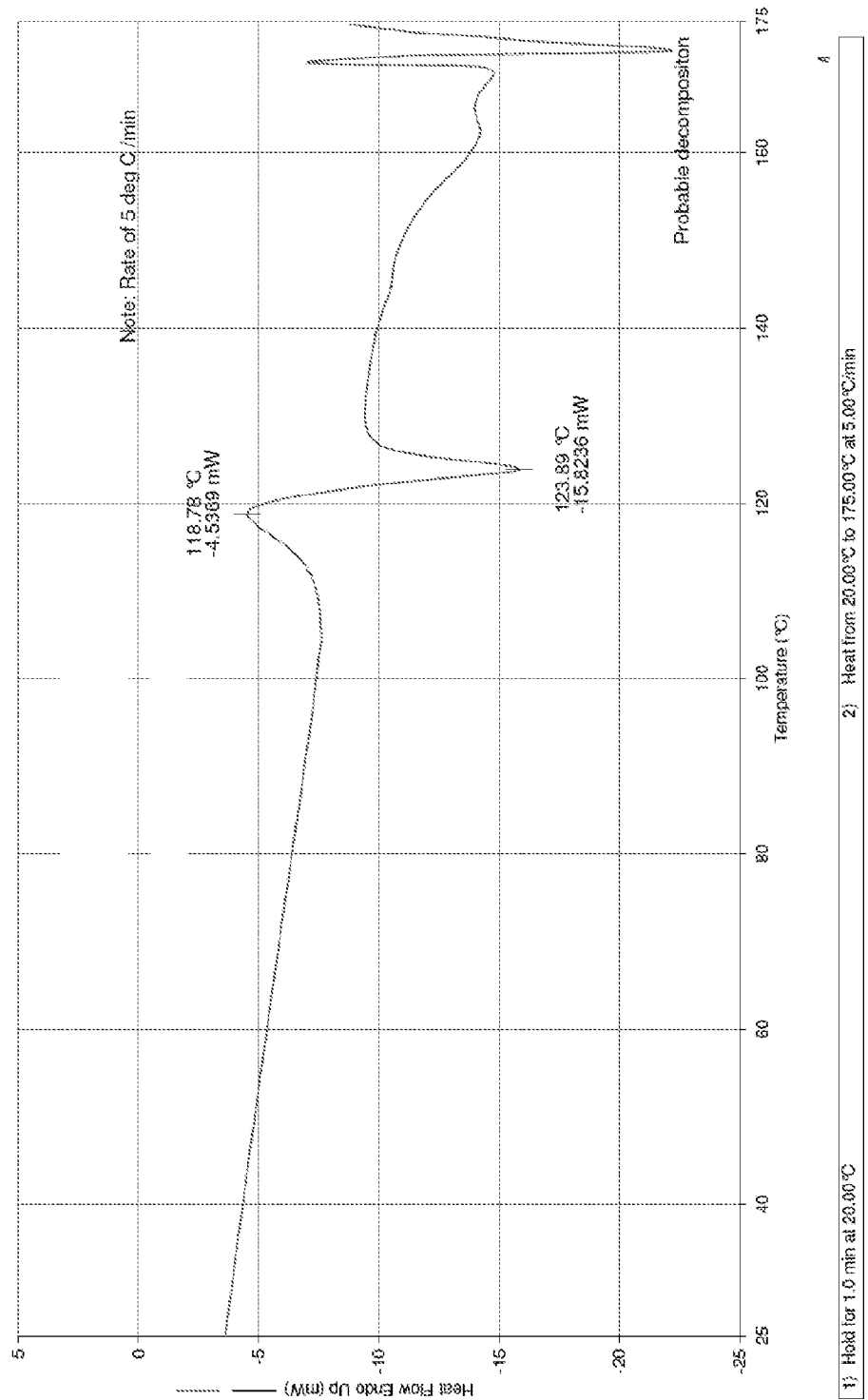
FIG. 2 shows a DSC thermogram of the crystalline nicotinamide riboside chloride at a heating rate of 5° C./min.

In some embodiments, the crystalline form of the invention has an endotherm of 123.9° C. in the DSC thermogram at a heating rate of 5° C./min. For example, the crystalline form of may have a DSC thermogram substantially as shown in FIG. 2.

Figure 3:
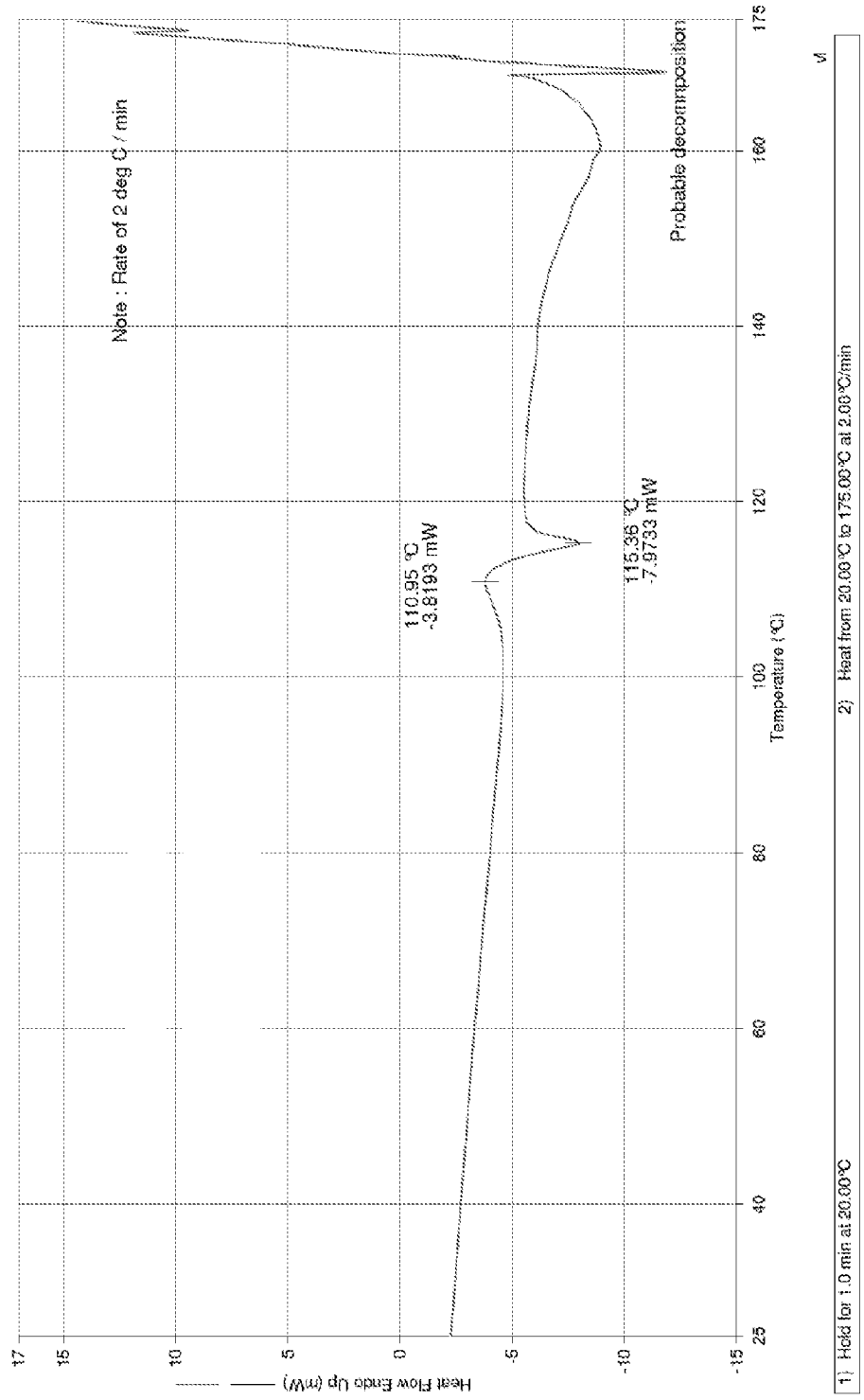
FIG. 3 shows a DSC thermogram of the crystalline nicotinamide riboside chloride at a heating rate of 2° C./min.

In other embodiments, the crystalline form of the invention has an endotherm of 115.4° C. in the DSC thermogram at a heating rate of 2° C./min. For example, the crystalline form of may have a DSC thermogram substantially as shown in FIG. 3.

Figure 4:
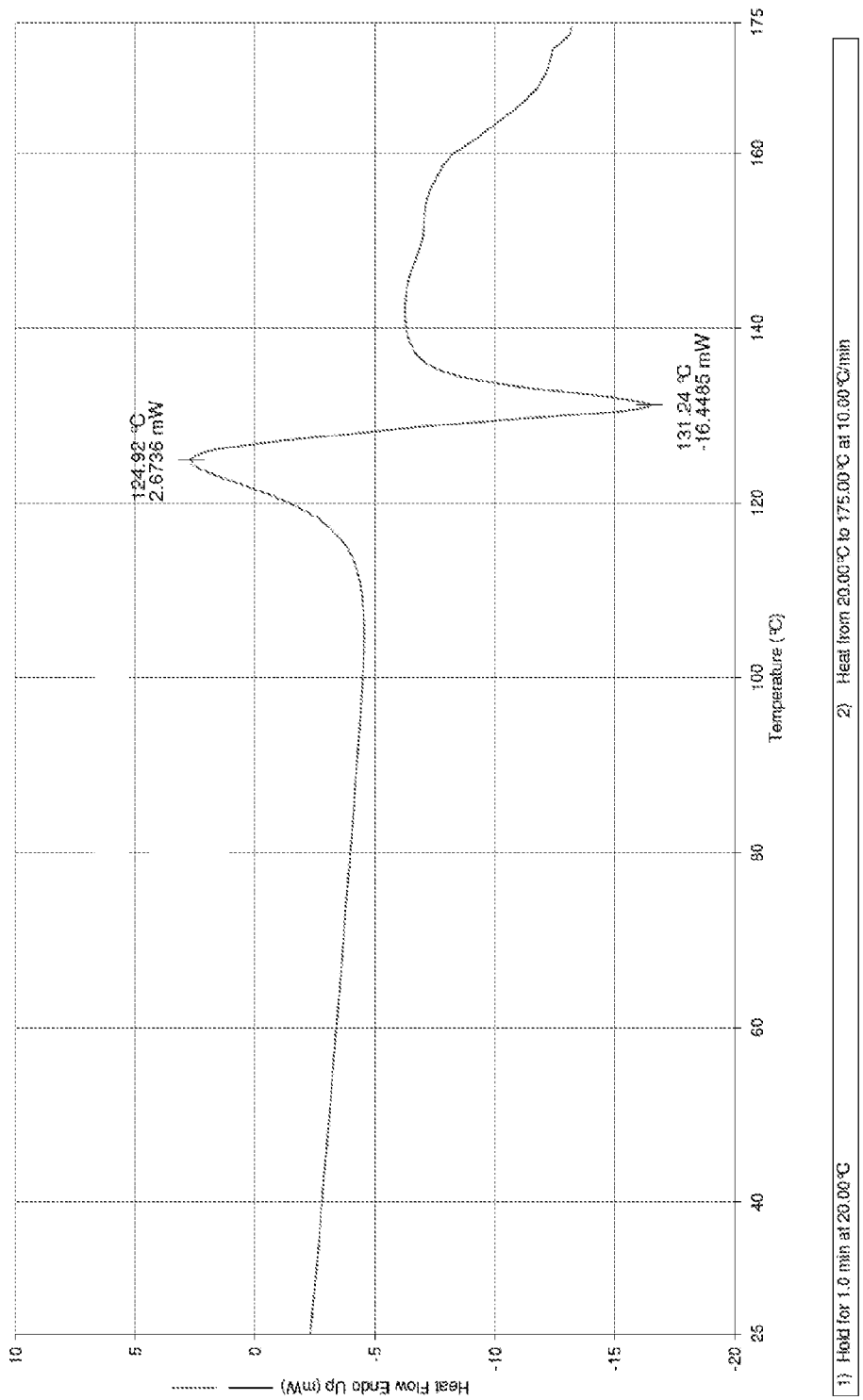
FIG. 4 shows a DSC thermogram of the crystalline nicotinamide riboside chloride at a heating rate of 10° C./min.

In other embodiments, the crystalline form of the invention has an endotherm of 131.2° C. in the DSC thermogram at a heating rate of 10° C./min. Such a crystal form may have a DSC thermogram substantially as shown in FIG. 4.

Figure 5:
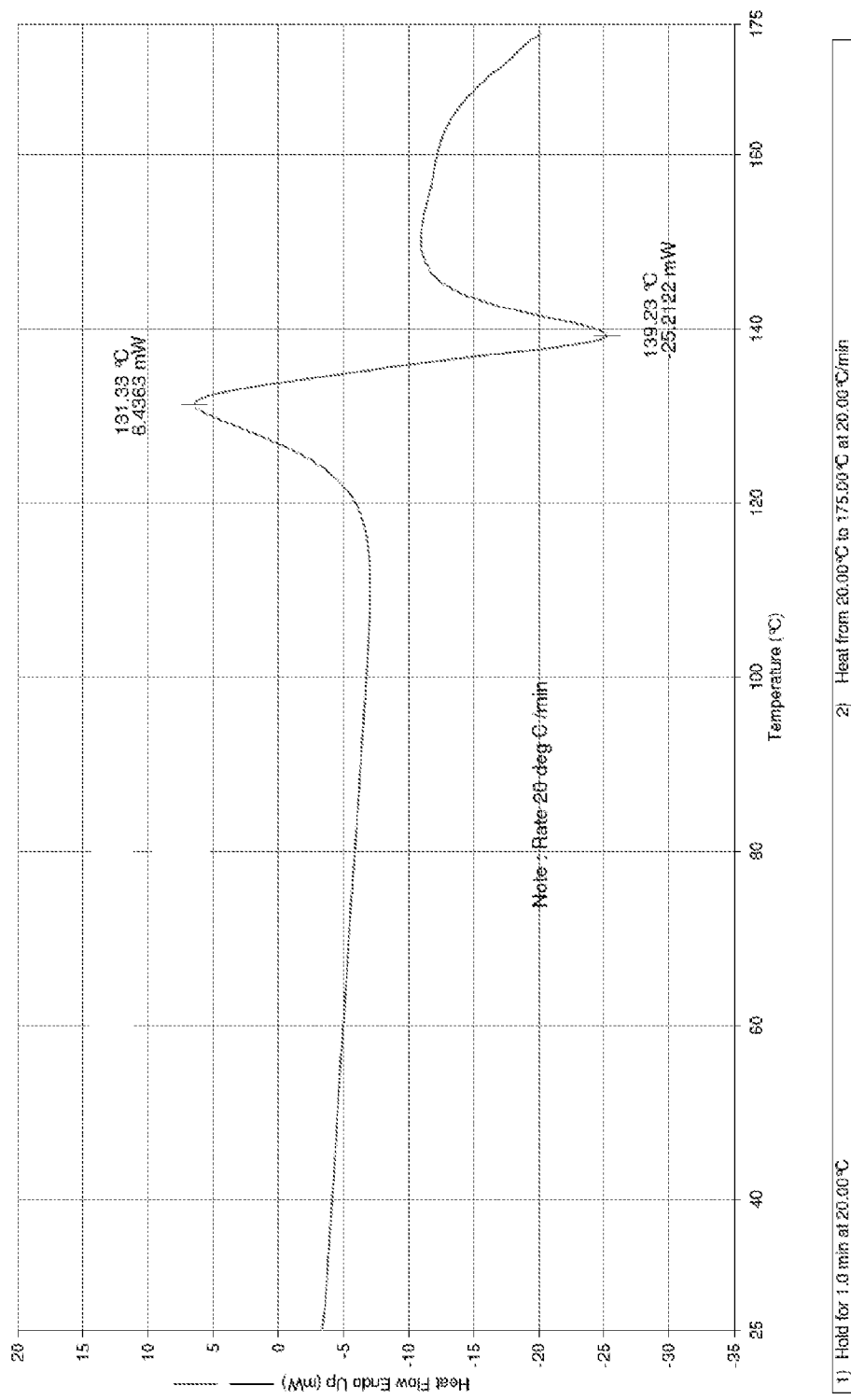
FIG. 5 shows a DSC thermogram of the crystalline nicotinamide riboside chloride at a heating rate of 20° C./min.

In some embodiments, the crystalline form of the invention has an endotherm of 139.2° C. in the DSC thermogram at a heating rate of 20° C./min. Such a crystal form may have a DSC thermogram substantially as shown in FIG. 5.

In certain such embodiments, the endotherm represents the melting point.

The crystalline form of the invention may have a purity of 95%, 96%, 97%, 98%, 99%, 99.2%, 99.4%, 99.6%, 99.8% or higher.

III. Synthetic Methods

In certain aspects, the present invention provides a method for preparing a crystalline form described herein, the method comprising (a) providing a mixture of a compound of formula (I) in a first organic solvent; and (b) crystallizing the compound of formula (I) from the mixture of a compound of formula (I) in a first organic solvent.

In certain embodiments, the first organic solvent is methanol.

In alternative embodiments, the first organic solvent is another polar protic solvent such as ethanol or isopropanol. Alternatively, the first organic solvent is a polar aprotic solvent, such as tetrahydrofuran, optionally in combination with water or an organic polar protic solvent.

In certain embodiments, the mixture comprising the compound of formula (I) and the first organic solvent is a solution, and the step of crystallizing the compound of formula (I) from the mixture comprises bringing the solution to supersaturation to cause the compound of formula (I) to precipitate out of solution.

In certain embodiments, the step of bringing the solution to supersaturation comprises slowly adding an anti-solvent, allowing the solution to cool, reducing the volume of the solution, or any combination thereof. In some embodiments, the step of bringing the solution to supersaturation comprises cooling the solution to ambient temperature or lower. Preferably, the step of bringing the solution to supersaturation comprises reducing the volume of the solution.

In certain embodiments, the method further comprises isolating the crystalline form, e.g. by filtering the crystals, by decanting fluid from the crystals, or by any other suitable separation technique.

In further embodiments, the preparation method further comprises washing the crystalline form with a second organic solvent. The second organic solvent may be selected from ethanol, acetone, methyl tert-butyl ether and combinations thereof.

The method can also comprise the step of drying the crystals, for example under reduced pressure.

A "polar protic solvent" as used herein is a solvent having a dipole moment of about 1.4 to 4.0 D, and comprising a chemical moiety that participates in hydrogen bonding, such as an O—H bond or an N—H bond. Exemplary polar protic solvents include methanol, ethanol, n-propanol, isopropanol, n-butanol, isobutanol, ammonia, water, and acetic acid.

A "polar aprotic solvent" as used herein means a solvent having a dipole moment of about 1.4 to 4.0 D that lacks a hydrogen bonding group such as O—H or N—H. Exemplary polar aprotic solvents include acetone, N,N-dimethylformamide, acetonitrile, ethyl acetate, dichloromethane, tetrahydrofuran, and dimethyl sulfoxide.

A "non-polar solvent" as used herein means a solvent having a low dialectric constant (<5) and low dipole moment of about 0.0 to about 1.2. Exemplary nonpolar solvents include pentane, hexane, cyclohexane, benzene, toluene, chloroform, and diethyl ether.

For purposes of this invention, the chemical elements are identified in accordance with the Periodic Table of the Elements, CAS version, Handbook of Chemistry and Physics, 67th Ed., 1986-87, inside cover.

Examples of alcohols include, without limitation, methanol, ethanol, 2-butoxyethanol, propanol, allyl alcohol, methallyl alcohol, prenol, isopropanol, 2,2-dimethylpropan-1-ol, 2-methyl-2-phenylpropan-1-ol, butanol, isobutanol, sec-butanol, tert-butanol, 2-buten-1-ol, pentanol, 2-cyclopenten-1-ol, 4-cyclopenten-1-ol, cyclopentanol, 3-cyclopenten-1-ol, hexanol, cyclohexanol, 3-cyclohexen-1-ol, phenol, 1-naphthol, 2-naphthol, benzyl alcohol, menthol, 1,2-ethanediol, 9-fluorenylmethanol, resorcinol, meta-cresol, cinnamyl alcohol, and geraniol.

IV. Compositions of the Invention

In certain embodiments, the invention provides a crystalline form of a compound having the structure of formula (I), described herein.

In certain embodiments, the purity of the crystalline form is 95%, 96%, 97%, 98%, 99%, 99.2%, 99.4%, 99.6%, 99.8% or higher.

In yet further embodiments, the present invention provides a pharmaceutical composition comprising a crystalline form of the invention in combination with a pharmaceutically acceptable carrier.

As described in detail below, the pharmaceutical compositions described herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; or (3) sublingually.

In some embodiments, the composition comprises additional agents. For example, the composition may comprise a nutritional agent, such as an antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations of the compounds described herein may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation described herein comprises an excipient, including, but not limited to, cyclodextrins, liposomes, micelle forming agents, e.g., bile acids, and polymeric carriers, e.g., polyesters and polyanhydrides; and an agent of the invention. In some embodiments, an aforementioned formulation renders orally bioavailable an agent of the invention. Methods of preparing these formulations or compositions may include the step of bringing into association a compound of the invention with the carrier and, optionally, one or more accessory ingredients.

Liquid dosage forms for oral administration of the formulations provided herein include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations provided herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound of the invention may also be administered as a bolus, electuary, or paste.

In solid dosage forms of the invention for oral administration (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions described herein may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Pharmaceutical compositions provided herein suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

V. Methods of Treatment

In certain embodiments, the present invention provides a method of improving cellular health in a subject, comprising administering to the subject a crystalline form disclosed herein.

In further embodiments, the present invention provides methods for:
 improving sleep quality;
 stimulating or increasing REM sleep;
 treating or preventing insomnia;
 treating or preventing desynchronosis; or
 treating or preventing a circadian rhythm sleep disorder in a subject, comprising administering to the subject a crystalline form disclosed herein.

In certain embodiments, such a method of treatment further comprises administering pterostilbene.

In some embodiments, the methods treat or prevent a circadian rhythm sleep disorder. The circadian rhythm sleep disorder can be extrinsic (e.g., shift work sleep disorder, desynchornosis) or intrinsic (e.g., advanced sleep phase disorder (ASPD), delayed sleep phase disorder (DSPD), irregular sleep-wake rhythm, and/or non-24-hour sleep-wake disorder (i.e., hypernychthemeral syndrome)).

The subject may be male or female. In some embodiments, the subject is an adult (i.e., 18 years of age or older). The subject may be pediatric (i.e., less than 18 years of age). In some embodiments, the subject is a mammal, preferably, a human.

In certain aspects, the methods and compositions provided herein relate to improving sleep health and the quality of sleep in a subject in a subject by administering to the subject (e.g., orally administering to the subject) a composition comprising crystalline nicotinamide riboside in the crystalline form described herein and/or pterostilbene. Sleep quality may refer to the "restfulness" of sleep (i.e., how rested an individual feels during waking hours). Sleep quality may refer to the quantity of sleep. Good sleep quality is associated with a wide range of positive outcomes such as better health, less daytime sleepiness, greater well-being and better psychological functioning. In some embodiments, a subject has a score of 1, 2, or 3 on the Pittsburgh Sleep Quality Index (PSQI). Further details on the PSQI may be found at Buysse, D. J., Reynolds, C. F., Monk, T. H., Berman, S. R., & Kupfer, D. J. (1989). The Pittsburgh Sleep Quality Index (PSQI): *A new instrument for psychiatric research and practice. Psychiatry Research,* 28(2), 193-213, incorporated herein by reference in its entirety. In some embodiments, the subject has trouble falling asleep. In some embodiments, the subject has trouble staying asleep. In some embodiments, the subject wakes in the morning at an hour that would disrupt a normal sleep cycle or otherwise affect sleep quality.

In some aspects, provided herein are methods of stimulating REM sleep in need thereof, comprising administering to the subject a crystalline form of the invention and/or pterostilbene. Rapid eye movement sleep (REM sleep) is a unique phase of sleep characterized by rapid movement of the eyes, low muscle tone throughout the body, and the propensity of the sleeper to dream vividly. In some embodiments, the compositions and methods disclosed herein increase the total amount of time a subject is in REM sleep per sleep session (e.g., the total amount of time in REM per night). In some embodiments, the compositions and methods disclosed herein increase the amount of time a subject is in REM sleep per sleep cycle. Sleep progresses in a series of four or five more or less regular sleep cycles of non-REM and REM sleep throughout the night. The first sleep cycle is typically around 90 minutes in length, with the succeeding cycles averaging around 100-120 minutes, although some individuals may have longer or shorter average cycles. Each cycle follows the stages of non-REM sleep (stage 1-stage 2-stage 3) and then, after a period in deep stage 3 slow-wave sleep, back through the stages (stage 3-stage 2-stage 1). Then, instead of waking, the sleeper may enter a short period of REM sleep, before going back through non-REM stages in a new cycle. As the night progresses, the time spent in deep stage 3 sleep decreases and the time spent in REM sleep increases, so that there is a greater proportion of stage 3 sleep earlier in the night, and a greater proportion of REM sleep later in the night, particularly during the final two sleep cycles. As used herein, stimulating REM or increasing REM may refer to increasing the time a subject stays in REM sleep per sleep cycle or the total amount of time a subject is sleeping per day.

In certain aspects, the methods and compositions provided herein relate to the treatment and/or prevention of sleep disorders in a subject by administering to the subject (e.g., orally administering to the subject) a crystalline form of the invention and/or pterostilbene.

In some embodiments, the subject has insomnia. Insomnia is a sleep disorder that is characterized by the inability to sleep. For example, a subject with insomnia may have trouble falling asleep, staying asleep, or wake up too early and not be able to get back to sleep. As used herein, insomnia may refer to short-term (acute) insomnia (i.e., the inability to sleep that lasts for days to weeks) or long-term (chronic) insomnia (i.e., the inability to sleep for one month or more). In some embodiments, the insomnia is transient insomnia. Insomnia may be the result of stress, a traumatic event, nasal/sinus allergies, gastrointestinal problems, brain lesions and tumors, stroke, chronic pain, chronic fatigue syndrome, congestive heart failure, angina, acid-reflux disease (GERD), chronic obstructive pulmonary disease, asthma, endocrine disorders such as hyperthyroidism, arthritis, neurological conditions such as Parkinson's or Alzheimer's disease, low back pain, or genetics. In some embodiments, the subject has restless leg syndrome. In some embodiments, the subject has sleep apnea. In some embodiments, the subject has a psychological condition that interferes with sleep, such as anxiety, depression, bipolar disorder, schizophrenia, posttraumatic stress disorder (PTSD), and/or attention deficit hyperactivity disorder (ADHD). In some embodiments, insomnia is a side effect of medication. Examples of medications that may cause insomnia include, but are not limited to, corticosteroids, alpha blockers, beta blockers, SSRI antidepressants, ACE inhibitors, cholinesterase inhibitors, second generation (non-sedating) HI agonists, or glucosamine/chondroitin.

Provided herein are methods and compositions useful in regulating a subject's circadian rhythm. Circadian rhythms regulate the timing of periods of sleepiness and wakefulness throughout the day. Circadian rhythms are endogenously generated, although they can be modulated by external cues such as sunlight and temperature. Circadian rhythms are important in determining the sleeping and feeding patterns of all animals, including human beings. There are clear patterns of brain wave activity, hormone production, cell regeneration and other biological activities linked to this daily cycle, and an irregular circadian rhythm may lead to a disturbance any of the previously mentioned processes. In some embodiments, the subject has a circadian rhythm sleep disorder. The circadian rhythm sleep disorder may be extrinsic (e.g., the result of environmental influences or circumstances) or intrinsic (e.g., the result of genetics or not the result of circumstances). An example of an extrinsic circadian sleep disorder includes shift work sleep disorder, which often affects individuals who work nights or in rotating shifts. Intrinsic sleep disorders include advanced sleep phase disorder (ASPD), delayed sleep phase disorder (DSPD), irregular sleep-wake rhythm, and/or non-24-hour sleep-wake disorder (i.e., hypernychthemeral syndrome)). ASPD is characterized by difficulty staying awake in the evening and difficulty staying asleep in the morning. DSPD is characterized by a much later than normal timing of sleep onset and offset and a period of peak alertness in the middle of the night. Individuals with irregular sleep-wake rhythm suffer from sleeping at very irregular times, and usually more than twice per day (waking frequently during the night and taking naps during the day), but often sleep a normal period of total time per day typical for the person's age. Non-24-hour sleep-wake disorder, or hypernychthemeral syndrome, is a sleep disorder wherein the affected individual's sleep occurs later and later each day, with the period of peak alertness also continuously moving around the clock from day to day.

In some aspects, the compositions and methods provided herein are useful in treating desynchronosis (i.e., jet lag). Jet lag is a temporary sleep disorder caused by crossing time zones (e.g., during an airplane flight), and is often the result of disruption to the circadian rhythms of the body. Jet lag may occur any time the body's internal clock is out of sync with cues from a new time zone. Cues can include light exposure and eating times. General symptoms include fatigue and disorientation, interrupted sleep, confusion, mood changes, and pain in limbs.

Actual dosage levels and administration regimen of the compositions disclosed herein may be varied so as to obtain an amount of nicotinamide riboside and/or pterostilbene that is effective to achieve the desired therapeutic response for a particular patient, composition, and mode of administration, without being toxic to the patient. In some embodiments, the subject continuously self-administers the compounds disclosed herein. In other embodiments, the subject may take a compound disclosed herein as needed.

In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). In some embodiments, the dose comprises at least 25 mg, at least 50 mg, at least 75 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 550 mg, at least 600 mg, at least 650 mg, at least 700 mg, at least 750 mg, at least 800 mg, or at least 850 mg nicotinamide riboside (compound 4). In some embodiments, the dose comprises at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 90 mg, at least 95 mg, at least 100 mg, at least 110 mg, at least 120 mg, at least 130 mg, at least 140 mg, at least 150 mg, at least 160 mg, least 170 mg, at least 180 mg, at least 190 mg, at least 200 mg, or at least 250 mg of pterostilbene.

The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

In further embodiments, the present invention provides methods of:
treating or preventing a motor neuron disease;
treating or preventing ALS; or
slowing or reversing the progression of motor neuron degeneration in a subject, comprising administering to the subject a crystalline form disclosed herein.

In certain embodiments, such a method of treatment further comprises administering pterostilbene.

In certain embodiments, the motor neuron disease is ALS, hereditary spastic paraplegia (HSP), primary lateral sclerosis (PLS), progressive muscular atrophy (PMA), progressive bulbar palsy (PBP), pseudobulbar palsy, or a spinal muscular atrophy.

In some embodiments, the subject may have or be predisposed to a motor neuron disease (e.g., amyotrophic lateral sclerosis (ALS), such as medulla ALS or brainstem ALS). A motor neuron disease or disorder may be any disease or disorder that affects the function or structure of motor neuron. As used herein, a motor neuron diseases include progressive diseases that result in loss of function of motor neurons, or nerves, in the brain and spinal cord. Examples of motor neuron diseases include amyotrophic lateral sclerosis (ALS), hereditary spastic paraplegia (HSP), primary lateral sclerosis (PLS), progressive muscular atrophy (PMA), progressive bulbar palsy (PBP), pseudobulbar palsy, or a spinal muscular atrophy. A motor neuron disease may affect the upper motor neurons or the lower motor neurons.

Actual dosage levels and administration regimen of the compositions disclosed herein may be varied so as to obtain an amount of nicotinamide riboside and/or pterostilbene that is effective to achieve the desired therapeutic response for a particular patient, composition, and mode of administration, without being toxic to the patient.

In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). In some embodiments, the dose comprises at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg, at least 2400 mg, at least 2500 mg, at least 2600 mg, at least 2700 mg, at least 2800 mg, at least 2900 mg, or at least 3000 mg, of nicotinamide riboside compound 4). In some embodiments, the dose comprises at least 5 mg, at least 10, at least 20 mg, at least 30 mg, at least 40 mg, at least 50 mg, at least 60 mg, at least 80 mg, at least 100 mg, at least 120 mg, at least 140 mg, at least 160 mg, at least 180 mg, at least 200 mg, at least 220 mg, at least 240 mg, at least 260 mg, at least 280 mg, at least 300 mg, at least 320 mg, at least 340 mg, at least 360 mg, at least 380 mg, at least 400 mg, at least 500 mg, at least 600 mg, at least 700 mg, at least 800 mg, at least 900 mg, or at least 1000 mg of pterostilbene.

The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

In some embodiments, the subject is given a test to measure the general progression or symptomatic progression of a motor neuron disease. In some embodiments, the subject is given a motor function test and/or a cognition and conduct function test. The motor function test may be Revised Amyotrophic Lateral Sclerosis Functional Rating Scale (ALSFRS-R). The cognition and conduct test may be Complutense Verbal Learning Test (TAVEC), Symbol Digit Modalities Test (SDMT), Verbal Fluency Test, Digit Span (Wechsler Memory Scale III), D2 Attention Test, Wechsler Memory Scale III for Letters and Numbers, London Tower Test, Stroop test, Frontal System Behavior Scale (FrSBe), and/or Brief Test (subjective conduct). In some embodiments, subjects are given both motor function and cognitive function tests. Motor function or cognitive functions tests may be given to the subject once or multiple times.

In some embodiments, the method further comprises measuring a feature (e.g., a feature associated with inflammation) in the subject. In some embodiments, the feature is measured in a blood test. Examples of features that may be tested are the level of a cytokine, level of amyloid A protein, level of macrophage activation marker neopterin, level of creatine phosphokinase (CPK), level of erythrocyte sedimentation rate, level of C-reactive protein, plasma viscosity, and/or white blood cell count. In some embodiments, the cytokine is proinflammatory cytokine. In some embodiments, the cytokine is an anti-inflammatory cytokine. Examples of cytokines include, but are not limited to, TNFα, IFNγ, IL-1, IL-6, IL-8, or TGFβ.

In some embodiments, the method further comprises administering a fatty acid supplement to the subject. In some embodiments, the fatty acid supplement comprises an oil. The oil may be processed (e.g., refined, bleached, or deodorized). In other embodiments, the oil is unprocessed or a virgin oil. In some embodiments, the fatty acid supplement is derived or fractionated from a source to yield separated fatty acids. In some embodiments, the oil is a coconut oil. Coconut oil, as used herein, may include any oil produced by the nut of the coconut palm. Fatty acids found in the supplements disclosed herein may be short-chain fatty acids, medium chain fatty acids, or long chain fatty acids. Exemplary fatty acids that may be found in the supplement include, but are not limited to, caproic acid, caprylic acid, capric acid, lauric acid, myristic acid, palmitic acid, palmitoleic acid, stearic acid, oleic acid, linoleic acid, and/or linolenic acid. The fatty acid supplement disclosed herein may comprise saturated fatty acids, unsaturated fatty acids, monounsaturated fatty acids, and/or polyunsaturated fatty acids. In some embodiments, the fatty acid supplement may comprise a hydrogenated oil. Fatty acid supplements may comprise one or more fatty acid(s). Actual dosage levels and administration regimen of the fatty acid supplement disclosed herein may be varied so as to obtain an amount of fatty acid supplement that is effective to achieve the desired therapeutic response for a particular patient, composition, and mode of administration, without being toxic to the patient.

In further embodiments, the present invention provides methods relating to:
 improving fertility;
 treating or preventing infertility;
 inducing ovulation;
 increasing sperm count; or
 increasing lactation;
comprising administering to the subject a crystalline form of the invention.

In certain embodiments, such a method of treatment further comprises administering pterostilbene.

In some embodiments, improving fertility or treating and/or preventing infertility comprises inducing ovulation and/or oocyte and follicle maturation in a female subject. In some embodiments, improving fertility or treating and/or preventing infertility comprising increasing sperm count and/or sperm motility in a male subject.

In some embodiments, the subject is a mammal (e.g., a human, a non-human mammal). The subject may be male or female. In some embodiments, the subject has impaired fertility (e.g., reduced sperm count, reduced sperm motility, reduced ovulation, reduced follicle and/or oocyte maturation). In some embodiments, the subject is infertile or sterile.

In some embodiments, provided herein are methods of increasing overall sperm health and/or sperm count in a subject by administering to the subject (e.g., a subject in need thereof) a composition disclosed herein. Increasing sperm count may be achieved by increasing the concentration of spermatozoa in seminal fluid, increasing the absolute number of spermatozoa in semen and/or increasing the volume of semen per ejaculate. The methods and compositions disclosed herein may increase overall sperm count by increasing or inducing spermatogenesis. In some embodiments, administering the compositions disclosed herein increase or improve sperm motility (e.g., increasing the percentage of spermatozoa moving in semen or increasing the amount of time spermatozoa are moving) in a subject. In some embodiments, administering the compositions disclosed herein maintains or improves overall sperm health, sperm count, and/or sperm motility in the testes and/or epididymis post spermatogenesis.

In some embodiments, provided herein are methods of inducing and/or increasing the likelihood of ovulation in a subject by administering to the subject (e.g., a subject in need thereof) a composition disclosed herein. In some embodiments, provided herein are methods of inducing follicle and oocyte maturation (e.g., folliculogenesis) in a subject by administering to the subject (e.g., a subject in need thereof) a composition disclosed herein.

Disclosed herein are compositions and methods to aid in in vitro fertilization procedures and practices. In some aspects, provide herein are methods of treating, preserving, or improving gamete (i.e., sperm and/or oocyte) likelihood of fertilization in an in vitro procedure. In some embodiments, compositions disclosed herein are added to semen (e.g., semen obtained from a donor subject) in preparation of for artificial insemination or intrauterine insemination (IUI). In some embodiments, compositions disclosed herein are added to semen in preparation intracytoplasic sperm injection into an oocyte.

In some embodiments, the compositions disclosed herein may be used to enhance mitochondrial numbers, mitochondrial activity, cellular energy levels or cellular energy-producing potential in oocytes, postnatal female germline stem cells (also referred to herein as OSCs) and/or preimplantation embryos prior to conducting and/or following methods of in vitro fertilization. It has been recently discovered that adult female mammals retain rare germline or oogonial stem cells (OSCs) that routinely produce new oocytes in a manner analogous to germline stem cell support of sperm production in the adult testis, and these OSCs may be new targets for in vitro fertilization therapies (Spradling, *Nature* 2004 428:133-134). In some embodiments, provided herein are methods of increasing the overall viability of an oocyte removed from a subject (e.g., an oocyte removed in preparation for in vitro fertilization). In some embodiments, an oocyte is treated or stored with a composition disclosed herein prior to in vitro fertilization. In one example, provided herein are methods of in vitro fertilization, the method involving the steps of: incubating an oocyte from a subject with a composition disclosed herein; and fertilizing the oocyte in vitro to form a zygote. In another example, the methods provided herein include a method of in vitro fertilization, the method involving the steps of (a) incubating an OSC from a subject with composition disclosed herein; (b) obtaining a composition containing OSC mitochondria from the OSC; (c) transferring the composition into an isolated oocyte (e.g., an oocyte extracted from a subject); and (d) fertilizing the oocyte in vitro to form a zygote.

In some embodiments, the composition disclosed herein may be added to a solution used for in vitro fertilization procedures for oocyte preparation and/or storage, such as cell culture medium, oocyte retrieval solution, oocyte washing solution, oocyte in vitro maturation medium, ovarian follicle in vitro maturation medium, oocyte in vitro fertilization medium, embryo culture medium, cleavage medium, vitrification solution, cryopreservation solution and/or embryo thawing medium.

Gametes may be stored for any period of time with the compositions disclosed herein before in vitro fertilization is performed.

In some aspects, provided herein are methods of increasing lactation in a subject by administering to the subject (e.g., a subject in need thereof) a composition disclosed herein. In some embodiments, increasing lactation comprising increasing the rate at which milk is secreted and/or produced from the mammary glands of a subject. In some embodiments, increasing lactation comprises increasing the volume of secreted milk in the subject. In some embodiments, the subject is a human. In some embodiments the subject is a non-human animal, such as a dairy animal (e.g., a cow, a buffalo, a goat, a sheep, a camel).

In some aspects, provided herein are methods of improving animal fecundity and/or breeding outcomes in animal husbandry by administering the compositions disclosed herein to a subject(s) (e.g., a non-human subject). In some embodiments, increasing litter size in a subject (e.g., a non-human subject, such as a domesticated animal). In some embodiments, the subject is a mammal. The subject may be a rodent, lagomorph, feline, canine, porcine, ovine, bovine, equine, or primate. For example, a composition disclosed herein may be administered to a female subject to increase number of offspring per litter or reproductive cycle. Alternately, the compositions disclosed herein may be administered to male subjects to increase spermatozoa production to obtain semen samples with increased virility for use in artificial insemination.

Actual dosage levels and administration regimen of the compositions disclosed herein may be varied so as to obtain an amount of nicotinamide riboside and/or pterostilbene that is effective to achieve the desired therapeutic response for a particular patient, composition, and mode of administration, without being toxic to the patient.

In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). In some embodiments, the dose comprises at least 25 mg, at least 50 mg, at least 75 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 550 mg, at least 600 mg, at least 650 mg, at least 700 mg, at least 750 mg, at least 800 mg, or at least 850 mg of nicotinamide riboside (compound 4). In some embodiments, the dose comprises at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 90 mg, at least 95 mg, at least 100 mg, at least 110 mg, at least 120 mg, at least 130 mg, at least 140 mg, at least 150 mg, at least 160 mg, least 170 mg, at least 180 mg, at least 190 mg, at least 200 mg, or at least 250 mg of pterostilbene.

The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

In further embodiments, the present invention provides methods relating to:
 treating or preventing kidney damage;
 treating or preventing acute kidney injury;
 treating or preventing kidney disease; or
 increasing blood flow to the kidneys;
comprising administering to the subject a crystalline form of the invention.

In certain embodiments, such a method of treatment further comprises administering pterostilbene.

In certain embodiments, the kidney damage is the result of cancer, decreased blood flood to the kidneys (i.e., ischemia), back up of urine in the kidneys, sepsis, trauma, autoimmune disease, drug-induced toxicity (e.g., non-steroidal anti-inflammatory (MAID) induced nephrotoxicity), lead poisoning, and/or severe dehydration.

In some embodiments, the acute kidney injury is the result of decreased blood flow to the kidneys (i.e., ischemic injury). Decreased blood flow to the kidneys may be a result of hypotension, blood loss, severe diarrhea, heat attack, heart failure, deceased heart function, organ failure, drug-induced nephrotoxicity (e.g., NSAID induced nephrotoxicity), allergic reactions, burns, trauma (e.g., blunt trauma), and/or surgery. In some embodiments, the acute kidney injury is the result of cancer (e.g., multiple myeloma), sepsis, vasculitis, interstitial nephritis, scleroderma, tubular necrosis, glomerulonephritis, or thrombotic microangiopathy. In some embodiments, the acute kidney injury is the result of blockage of the urinary tract. Blockage of the urinary tract may be caused by bladder cancer, prostate cancer, cervical cancer, an enlarged prostate, kidney stones, or blood clots in the urine.

In some embodiments, the chronic kidney disease is the result of an immune system disease (e.g., lupus), long term viral disease (e.g., HIV/AIDS, hepatitis B, or hepatitis C), urinary tract infections, polycystic kidney disease, and/or inflammation of glomeruli.

As used herein, kidney damage may refer to a medical condition of impaired kidney function in which the kidneys fail to adequately filter metabolic wastes from the blood. In some embodiments, kidney damage is also indicative of kidney failure. Examples of conditions that may cause kidney damage include, but are not limited to decreased blood flood to the kidneys, back up of urine in the kidneys, sepsis, trauma (e.g., such as blunt trauma), an autoimmune disease, drug-induced nephrotoxicity (e.g., NSAID induced nephrotoxicity), heavy mental poisoning (e.g., lead poisoning), or severe dehydration.

In some aspects, provided herein are methods of treating or preventing acute kidney injury (i.e., in a subject in need thereof). In some embodiments, acute kidney injury is an episode of kidney failure or kidney damage that happens within a few hours or a few days. Acute kidney injury, as used herein, may be characterized by abrupt deterioration in kidney function. In some embodiments, the subject has acute kidney injury, and the acute kidney injury may manifest by an increase in serum creatinine level with or without reduced urine output. In some embodiments, the subject has increased serum creatinine levels. In some embodiments, the subject may have reduced urine output. In some embodiments, the subject has acute kidney injury, and the acute kidney injury may be prerenal (e.g., caused by decreased renal blood flow), intrinsic renal (e.g., caused by a process within the kidneys), or postrenal (e.g., caused by inadequate drainage of urine distal to the kidneys). Acute kidney injury or kidney damage may be a result of use (e.g., overuse) of medications, such as NSAIDs, angiotensin-converting enzyme inhibitors, angiotensin receptor blockers, cyclosporine, diuretics, tacrolimus, penicillin analogues, cephalosporins, sulfonamides, ciprofloxacin, acyclovir, rifampin, phenytoin, interferon, or proton pump inhibitors. Other causes of acute kidney injury and kidney damage include cardiorenal syndrome, hepatorenal syndrome, abdominal compartment syndrome, hypercalcemia, sepsis, neurogenic shock, infections of the renal parenchyma, glomerulonephritis, viral infections (such as Epstein-Barr virus infections or cytomegalovirus infections), bacterial infections (e.g., bacterial infections caused by bacteria of the *Streptococcus* or *Legionella* species), or fungal infections (e.g., fungal infections caused by candidiasis or histoplasmosis). In some embodiments, the acute renal injury and/or kidney damage is caused by a systemic disease, such as sarcoidosis or lupus.

Additional examples of conditions that cause acute kidney injury and kidney damage include cancer (e.g., multiple myeloma), prolonged hypotension, renal vein thrombosis, malignant hypertension, scleroderma renal crisis, renal atheroembolic disease, renal infarction vasculitis, interstitial nephritis, scleroderma, and or conditions that cause inflammation of or damage to the kidney tubules, such as tubular necrosis, glomerulonephritis, or thrombotic microangiopathy.

In some embodiments, the acute kidney injury and/or kidney damage is caused by a decrease in blood flow to the kidney. Conditions that may cause a decrease in blood flow to the kidneys includes, for example, blood loss, severe diarrhea, heat attack, heart failure, deceased heart function, organ failure, allergic reactions, burns, and/or trauma. In some embodiments, the subject has undergone surgery, and the subject's blood vessels have been clamped, leading to a decrease of blood flow to the kidneys. In some embodiments, the acute kidney injury or kidney damage is the result of a blockage of the urinary tract. A blockage of the urinary tract may be the result of, for example, neurogenic bladder, retroperitoneal fibrosis, bladder cancer, prostate cancer, cervical cancer, an enlarged prostate, kidney stones, blood clots, or tumors.

In some embodiments, the subject has a kidney disease. A kidney disease is any condition that affects the kidney's ability to filter compounds out of blood, filter extra water out of blood, and/or help control blood pressure. Kidney disease may be caused by diabetes, hypertension, a systemic disease (e.g., lupus), viral disease (e.g., HIV/AIDS, hepatitis B, or hepatitis C), urinary tract infections, a genetic disease, such as polycystic kidney disease, or any condition that results in the inflammation of kidney glomeruli.

In some embodiments, the subject's kidney function may be measured prior, during or after administration of a composition disclosed herein. Kidney function may be evaluated as a function of glomerular filtration rate, urine output, or the level of other biomedical markers of kidney health, such as creatinine, urea, nitrogen, phosphorus, or potassium. Markers such as creatinine, urea, nitrogen, phosphorus, or potassium may be measured in the urine or through a blood test.

Actual dosage levels and administration regimen of the compositions disclosed herein may be varied so as to obtain an amount of nicotinamide riboside and/or pterostilbene that is effective to achieve the desired therapeutic response for a particular patient, composition, and mode of administration, without being toxic to the patient.

In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). In some embodiments, the dose comprises at least 25 mg, at least 50 mg, at least 75 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 550 mg, at least 600 mg, at least 650 mg, at least 700 mg, at least 750 mg, at least 800 mg, or at least 850 mg of nicotinamide riboside (Compound 4). In some embodiments, the dose comprises at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 90 mg, at least 95 mg, at least 100 mg, at least 110 mg, at least 120 mg, at least 130 mg, at least 140 mg, at least 150 mg, at least 160 mg, least 170 mg, at least 180 mg, at least 190 mg, at least 200 mg, or at least 250 mg of pterostilbene. The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

In further embodiments, the present invention provides methods relating to treating and/or preventing liver related diseases and disorders and for improving liver health in a subject by administering to the subject a crystalline form disclosed herein. Specifically, the invention provides a method of:

treating or preventing liver damage;
treating or preventing fatty liver;
decreasing the serum level of alanine transaminase (ALT); or decreasing the serum level of aspartate transaminase (AST) in a subject;
comprising administering to the subject a crystalline form disclosed disclosed herein.

In certain embodiments, such a method of treatment further comprises administering pterostilbene.

In certain embodiments, the liver damage is the result of cancer (e.g., liver cancer, bile duct cancer and/or a liver adenoma), cirrhosis, viral infection (e.g., hepatitis A infection, a hepatitis B infection and/or a hepatitis E infection), congenital disorders of metabolism, trauma, autoimmune disease (e.g., autoimmune hepatitis, primary biliary cirrhosis, or primary sclerosing cholangitis), hemochromatosis, hyperoxaluria, oxalosis, Wilson's disease and/or drug-induced hepatotoxicity (e.g., alcohol-induced hepatotoxicity and/or acetaminophen-induced hepatotoxicity).

Provided herein are methods of preventing or treating liver damage and/or fatty liver in a subject by administering to the subject (e.g., a subject in need thereof) a composition disclosed herein.

In some embodiments, the subject may have or be predisposed to liver damage and/or fatty liver. Liver damage may result from any condition that causes the cells of the liver (i.e., hepatocytes) to die or otherwise not function normally. Examples of conditions that may cause liver damage include, but are not limited to, cancer (e.g., liver cancer, bile duct cancer, or a liver adenoma), trauma, congenital metabolic disorders (e.g., genetic metabolic disorders resulting in an enzyme deficiency), vascular injury, cirrhosis, a viral infection (e.g., hepatitis A, hepatitis B, hepatitis E), an autoimmune disease (e.g., autoimmune hepatitis, primary biliary cirrhosis, or primary sclerosing cholangitis), hemochromatosis, hyperoxaluria, oxalosis, Wilson's disease, or drug-induced hepatotoxicity (e.g., alcohol-induced hepatotoxicity or acetaminophen-induced hepatotoxicity). Fatty liver may be caused by any condition that causes fat accumulation of liver. These conditions may be, but are not limited to, non-alcoholic fatty liver disease or alcoholic liver disease.

Disclosed herein are methods of treating or preventing age-related symptoms or diseases comprising administering a composition disclosed herein. Provided herein are methods of decreasing the amount of alanine transaminase (ALT) and/or aspartate transaminase (AST) in a subject comprising administering to the subject a composition provided herein. AST and ALT are reasonably sensitive indicators of liver damage or injury from different types of diseases or conditions, and they are often measured in liver tests or liver blood tests. Elevated levels of AST and ALT are associated with liver damage and liver malfunction. In some embodiments, ALT is decreased in the subject by at least 0.1 U/L, at least 0.2 U/L, at least 0.3 U/L, at least 0.4 U/L, at least 0.5 U/L, at least 0.6 U/L, at least 0.7 U/L, at least 0.8 U/L, at least 0.9 U/L, at least 01.0 U/L, 1.1 U/L, at least 1.2 U/L, at least 1.3 U/L, at least 1.4 U/L, at least 1.5 U/L, at least 1.6 U/L, at least 1.7 U/L, at least 1.8 U/L, at least 1.9 U/L, at least 2.0 U/L, 2.1 U/L, at least 2.2 U/L, at least 2.3 U/L, at least 2.4 U/L, at least 2.5 U/L, at least 2.6 U/L, at least 2.7 U/L, at least 2.8 U/L, at least 2.9 U/L, at least 3.0 U/L, at least 3.5 U/L, 4.0 U/L, at least 4.5 U/L, or at least 5.0 U/L after administration of the composition. In some embodiments, the ALT is decreased by at least 0.1 U/L, at least 0.2 U/L, at least 0.3 U/L, at least 0.4 U/L, at least 0.5 U/L, at least 0.6 U/L, at least 0.7 U/L, at least 0.8 U/L, at least 0.9 U/L, at least 01.0 U/L, 1.1 U/L, at least 1.2 U/L, at least 1.3 U/L, at least 1.4 U/L, at least 1.5 U/L, at least 1.6 U/L, at least 1.7 U/L, at least 1.8 U/L, at least 1.9 U/L, at least 2.0 U/L, 2.1 U/L, at least 2.2 U/L, at least 2.3 U/L, at least 2.4 U/L, at least 2.5 U/L, at least 2.6 U/L, at least 2.7 U/L, at least 2.8 U/L, at least 2.9 U/L, at least 3.0 U/L, at least 3.5 U/L, 4.0 U/L, at least 4.5 U/L, or at least 5.0 U/L after administration of the composition.

Nicotinamide adenine dinucleotide (NAD$^+$) is a coenzyme that participates in many metabolic reactions. NAD+ plays an important role in transcription regulation, longevity, and age-associated diseases. NAD+ levels decrease with age, while increased NAD+ levels are associated with robust health. In some embodiments, provided herein are methods of increasing the amount of NAD+ of a subject by administering a composition disclosed herein. NAD+ may increase by at least 1.0 μg/mL, at least 2.0 μg/mL, at least 3.0 μg/mL, at least 4.0 μg/mL, at least 5.0 μg/mL, at least 6.0 μg/mL, at least 7.0 μg/mL, at least 8.0 μg/mL, at least 9.0 μg/mL, at least 10.0 μg/mL, at least 11.0 μg/mL, at least 12.0 μg/mL, at least 13.0 μg/mL, at least 14.0 μg/mL, at least 15.0 μg/mL, at least 16 μg/mL, at least 17 μg/mL, at least 18 μg/mL, at least 19 μg/mL, at least 20 μg/mL, at least 21 μg/mL, at least 22 μg/mL, at least 23 μg/mL, at least 24 μg/mL, at least 25 μg/mL, at least 26 μg/mL, at least 27 μg/mL, at least 28 μg/mL, at least 29 μg/mL, or at least 30 μg/mL after administration of the composition.

Provided herein are methods of decreasing blood pressure (e.g., diastolic blood pressure) of a subject by administering a composition herein. In some embodiments, the subject's diastolic blood pressure decreases by at least 1 mmHg, at least 1.5 mmHg, at least 2 mmHg, at least 2.5 mmHg, at least 3 mmHg, at least 3.5 mmHg, at least 4.0 mmHg, at least 4.5 mmHg, or at least 5 mmHg after administration of the composition.

In certain embodiments, the invention also provides a method of treating a disease comprising administering to a subject a crystalline form of the invention.

In certain such embodiments, the disease is a neurodegenerative disease. Exemplary neurodegenerative diseases include Alzheimer's, Parkinson's, and Huntington's Disease.

In alternative such embodiments, the disease is a skin disorder. Skin disorders may be caused by exposure to the sun; exemplary such disorders are selected from the group consisting of actinic keratoses, lentigines or age spots, seborrheic keratoses, sun burn, photosensitivity, moles, polymorphous light eruption, solar elastosis or wrinkles, skin cancer (such as melanoma, squamous cell carcinoma, and basal cell carcinoma), and freckles. Skin disorders may also be caused by inflammation; exemplary such disorders are selected from the group consisting of psoriasis, contact dermatitis, atopic dermatitis, seborrheic dermatitis, asteatotic eczema, discoid eczema, hand eczema, gravitational/varicose eczema, eczematous drug eruptions, lichen simplex, acne, lichen planus, pityriasis lichenoides, keratosis lichenoides chronica, lichen nitidus, lichen striatus, mycosis fungoides, erythroderma, erythema multiforme, Stevens-Johnson Syndrome, vasculitis, and toxic epidermal necrolysis. In further embodiments, a skin disorder may be caused by autoimmune disease is selected from the group consisting of pyoderma gangrenosum, systemic lupus erythematosus, eosinophilic fasciitis, scleroderma, pemphigus vulgaris, bullous pemphigoid, alopecia areata, vitiligo, psoriasis, dermatomyositis, and dystrophic epidermolysis bullosa.

In yet alternative embodiments, the disease is obesity or diabetes. The methods may also enable lipid lowering and blood pressure reduction.

In further alternative embodiments, the disease is muscle wasting or sarcopenia.

In further alternative embodiments, the disease is an autoimmune disease such as arthritis or lupus.

In further alternative embodiments, the disease is mitochondrial dysfunction or disease.

In still further alternative embodiments, the disease is an accelerated aging disease such as progeria.

In other embodiments, the disease is chemotherapy induced neuropathy, or cognitive decline. The methods may also enable pain reduction.

In yet further alternative embodiments, the disease is a cancer such as breast cancer, colon cancer, etc.

In other embodiments, the invention provides methods that promote sirtuin activation, NAD+ boosting, PARP activation, autophagy and mitophagy, or mitochondrial biogenesis.

In still further embodiments, the invention provides methods of promoting wellness comprising administering to a subject the crystalline form of the invention.

In some embodiments, the methods promote wellness by promoting stem cell health and function; such stem cells may be intestinal, skin, muscle, hematopoietic, or neural stem cells.

The methods may also promote wellness by preventing hearing loss or hair loss.

Alternatives, the methods may promote healthy hair and nail growth.

In yet further alternative embodiments, the methods may promote muscle building for endurance and strength, weight loss, or and increased immune response (innate and adaptive function).

Actual dosage levels and administration regimen of the compositions disclosed herein may be varied so as to obtain an amount of nicotinamide riboside (or nicotinamide riboside chloride) and/or pterostilbene that is effective to achieve the desired therapeutic response for a particular patient, composition, and mode of administration, without being toxic to the patient.

In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). In some embodiments, the dose comprises at least 25 mg, at least 50 mg, at least 75 mg, at least 100 mg, at least 125 mg, at least 150 mg, at least 200 mg, at least 225 mg, at least 250 mg, at least 275 mg, at least 300 mg, at least 325 mg, at least 350 mg, at least 375 mg, at least 400 mg, at least 425 mg, at least 450 mg, at least 475 mg, at least 500 mg, at least 550 mg, at least 600 mg, at least 650 mg, at least 700 mg, at least 750 mg, at least 800 mg, or at least 850 mg of nicotinamide riboside. In some embodiments, the dose comprises at least 5 mg, at least 10 mg, at least 15 mg, at least 20 mg, at least 25 mg, at least 30 mg, at least 35 mg, at least 40 mg, at least 45 mg, at least 50 mg, at least 55 mg, at least 60 mg, at least 65 mg, at least 70 mg, at least 75 mg, at least 80 mg, at least 90 mg, at least 95 mg, at least 100 mg, at least 110 mg, at least 120 mg, at least 130 mg, at least 140 mg, at least 150 mg, at least 160 mg, least 170 mg, at least 180 mg, at least 190 mg, at least 200 mg, or at least 250 mg of pterostilbene.

The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

In any of the treatment methods described herein, nicotinamide riboside chloride, alone or in combination with pterostilbene, may be formulated together with one or more pharmaceutically acceptable carriers (additives) and/or diluents. In another aspect, the agents described herein can be administered as such, or administered in mixtures with pharmaceutically acceptable carriers and can also be administered in conjunction with other agents. Conjunctive therapy thus includes sequential, simultaneous and separate, or co-administration of one or more compounds of the invention, wherein the therapeutic effects of the first administered has not entirely disappeared when the subsequent compound is administered.

Compositions useful for the methods of the invention are described above.

EXEMPLIFICATION

The invention described generally herein will be more readily understood by reference to the following examples, which are included merely for purposes of illustration of certain aspects and embodiments of the present invention, and are not intended to limit the invention.

Example 1. Scale-Up Synthesis and Crystallization of Nicotinamide Riboside Chloride

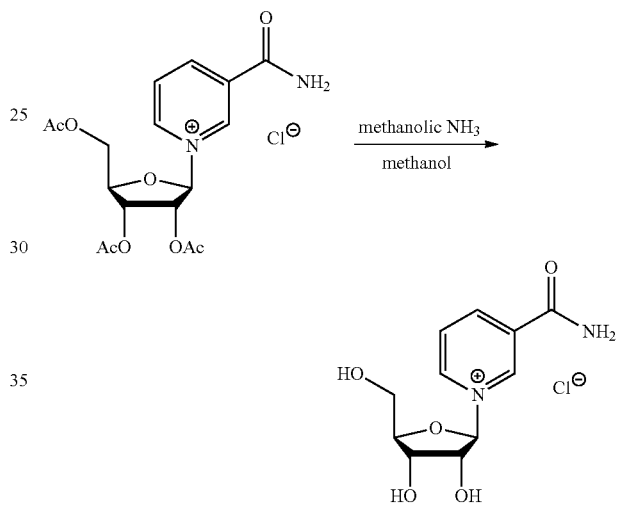

Figure 6:
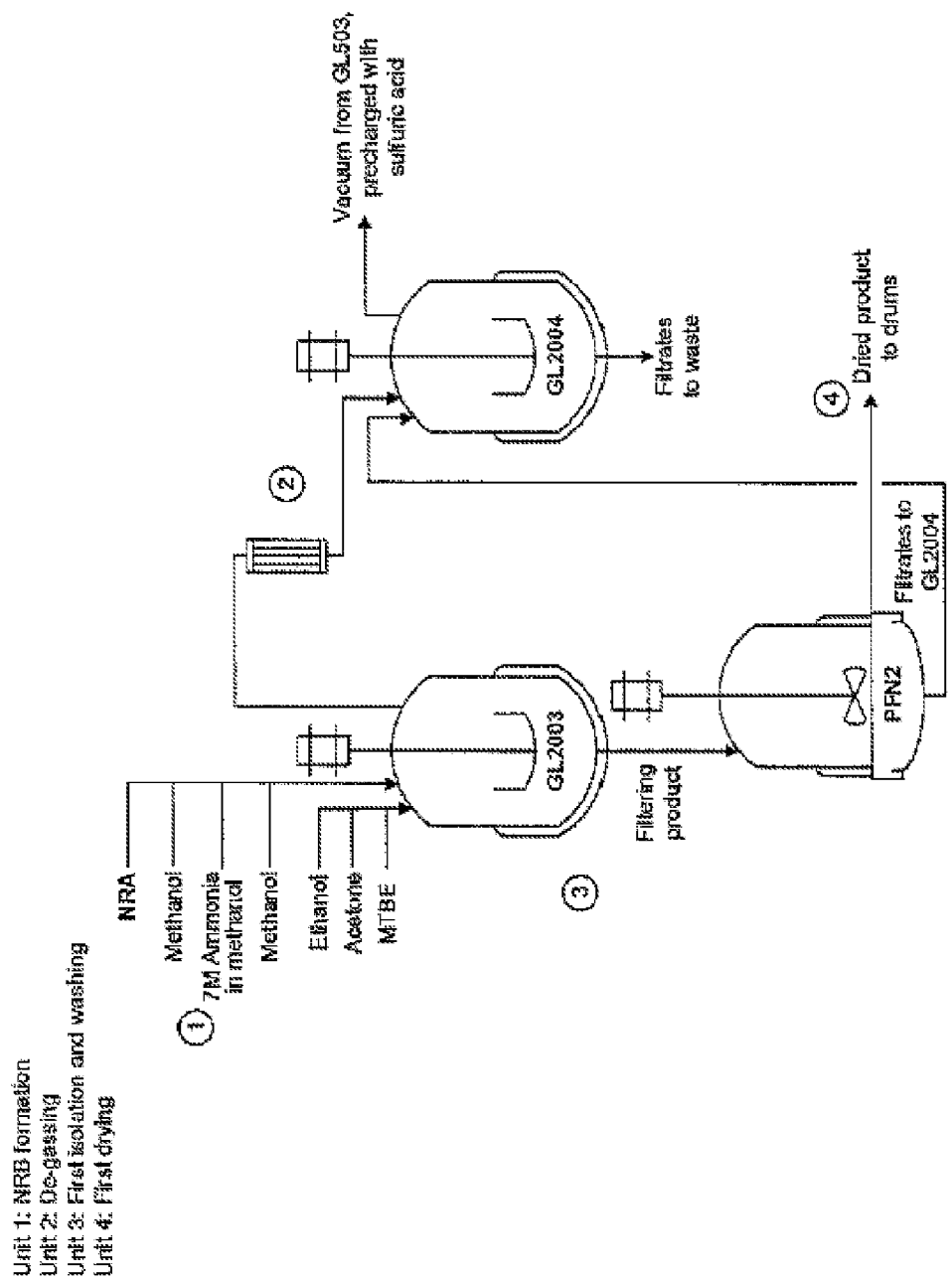
FIG. 6 shows a process flow diagram for the manufacture of the crystalline form of nicotinamide riboside chloride.

900 kg of nicotinamide riboside triacetate and 2133 kg of methanol were charged to a reactor and mixed, then cooled to 0° C. 747 kg of 7M mmmonia in methanol (i.e., "methanolic $NH_3$") was slowly charged to the reactor at 0° C. The reaction mixture was passed through a polish filter, then the reaction mixture was stirred for 14 hours. A sample from the reaction mixture was taken to assess reaction progress. Upon completion of the reaction, the reaction mixture was placed under vacuum, then warmed to 20° C. to 25° C. for 4 hours. Vacuum was applied until solids formed. Once solids were formed, the resultant slurry was filtered on a Nutsche filter dryer. Solids were washed with 1422 kg of ethanol, then 1422 kg of acetone, then 1322 kg of methyl tert butyl ether (MTBE). The resultant solids were then dried at 40° C. Product was formed with 60% yield. The process flow diagram for this reaction is shown in FIG. 6.

Example 2. Optional Secondary Isolation

The crystalline form may optionally undergo a second isolation process according to the following steps: The solids obtained in Example 1 were dissolved in purified water at 30° C. Ethanol was slowly added to the solution and mixed for 10 hours, over which time the solids began to precipitate. MTBE was then added and mixed for 2 hours. The mixture was then filtered on a Buchner funnel, and the solids were washed with ethanol, then acetone, then MTBE. Solids were dried at 40° C.

Example 3. Spectroscopic Data

The crystalline form made by the process described in Examples 1 and 2 has an XRD spectrum substantially as shown in FIG. 1. The instrument utilized in collecting the XRD data is a Rigaku Smart Lab X-Ray diffraction system.

Specifically, in order to collect the XRD data, The Rigaku Smart-Lab X-ray diffraction system was configured for reflection Bragg-Brentano geometry using a line source X-ray beam. The X-ray source is a Cu Long Fine Focus tube that was operated at 40 kV and 44 mA. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of 0.1° 2θ or less. The axial divergence of the X-ray beam is controlled by 5.0-degree Soller slits in both the incident and diffracted beam paths.

The samples were prepared in a low background Si holder using light manual pressure to keep the sample surface flat and level with the reference surface of the sample holder. The single crystal Si low background holder has a small circular recess (10 mm diameter and about 0.2 mm depth) that held between 20 and 25 mg of the sample. The samples were analyzed from 2 to 40 °2θ using a continuous scan of 6 °2θ per minute with an effective step size of 0.02 °2θ. The data collection procedure used to analyze these samples was not validated. The peak lists were generated using PDXL2 v.2.3.1.0. The figures were created using PlotMon V1.00.

INCORPORATION BY REFERENCE

All publications and patents mentioned herein are hereby incorporated by reference in their entirety as if each individual publication or patent was specifically and individually indicated to be incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

What is claimed is:

1. A crystalline form of a compound having the structure of formula (I):

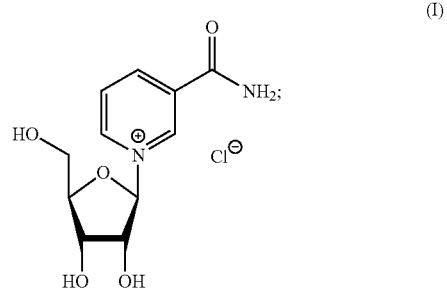

wherein the crystalline form is characterized by 2θ values of 20.9±0.1, 21.6±0.1, 21.8±0.1, 23.6±0.1, and 24.4±0.1.

2. The crystalline form of claim 1, characterized by 2θ values of 9.9±0.1, 18.4±0.1, 20.9±0.1, 21.6±0.1, 21.8±0.1, 23.6±0.1, 24.4±0.1, 29.4±0.1, 29.9±0.1, 30.5±0.1, and 33.5±0.1.

3. The crystalline form of claim 2, characterized by 2θ values of 9.9±0.1, 18.4±0.1, 20.9±0.1, 21.6±0.1, 21.8±0.1, 22.9±0.1, 23.6±0.1, 24.4±0.1, 25.2±0.1, 29.4±0.1, 29.9±0.1, 30.5±0.1, 31.9±0.1, 32.1±0.1, 33.5±0.1, 34.1±0.1, and 37.4±0.1.

4. The crystalline form of claim 3, characterized by 2θ values of 9.9±0.1, 15.6±0.1, 18.4±0.1, 18.5±0.1, 19.0±0.1, 20.9±0.1, 21.6±0.1, 21.8±0.1, 22.9±0.1, 23.6±0.1, 24.4±0.1, 25.2±0.1, 29.4±0.1, 29.9±0.1, 30.5±0.1, 31.5±0.1, 31.9±0.1, 32.1±0.1, 33.5±0.1, 34.0±0.1, 34.1±0.1, 36.5±0.1, and 37.4±0.1.

5. The crystalline form of claim 1, characterized by 2θ values of 20.87±0.10, 21.55±0.10, 21.79±0.10, 23.63±0.10, and 24.44±0.10.

6. The crystalline form of claim 5, characterized by 2θ values of 9.87±0.10, 18.36±0.10, 20.87±0.10, 21.55±0.10, 21.79±0.10, 23.63±0.10, 24.44±0.10, 29.35±0.10, 29.93±0.10, 30.47±0.10, and 33.51±0.10.

7. The crystalline form of claim 6, characterized by 2θ values of 9.87±0.10, 18.36±0.10, 20.87±0.10, 21.55±0.10, 21.79±0.10, 22.87±0.10, 23.63±0.10, 24.44±0.10, 25.25±0.10, 29.35±0.10, 29.93±0.10, 30.47±0.10, 31.87±0.10, 32.08±0.10, 33.51±0.10, 34.15±0.10, and 37.38±0.10.

8. The crystalline form of claim 7, characterized by 2θ values 9.87±0.10, 15.61±0.10, 18.36±0.10, 18.49±0.10, 19.01±0.10, 20.87±0.10, 21.55±0.10, 21.79±0.10, 22.87±0.10, 23.63±0.10, 24.44±0.10, 25.25±0.10, 29.35±0.10, 29.93±0.10, 30.47±0.10, 31.46±0.10, 31.87±0.10, 32.08±0.10, 33.51±0.10, 34.00±0.10, 34.15±0.10, 36.53±0.10, and 37.38±0.10.

9. The crystalline form of claim 1, having an XRD spectrum substantially as shown in FIG. 1.

10. The crystalline form of claim 1, having an endotherm of 123.9° C. in the DSC thermogram at a heating rate of 5° C./min.

11. The crystalline form of claim 1, having an endotherm of 115.4° C. in the DSC thermogram at a heating rate of 2° C./min.

12. The crystalline form of claim 1, having an endotherm of 131.2° C. in the DSC thermogram at a heating rate of 10° C./min.

13. The crystalline form of claim 1, having an endotherm of 139.2° C. in the DSC thermogram at a heating rate of 20° C./min.

14. The crystalline form of claim 1, wherein the purity of the crystalline form is 95%, 96%, 97%, 98%, 99%, 99.2%, 99.4%, 99.6%, 99.8% or higher.

\* \* \* \* \*